(12) United States Patent
Miller

(10) Patent No.: US 6,530,891 B2
(45) Date of Patent: Mar. 11, 2003

(54) MULTIPLE BIOPSY DEVICE

(75) Inventor: Larry Sherwin Miller, Bala Cynwyd, PA (US)

(73) Assignee: Temple University of the Commonwealth System of Higher Education, Philadelphia, PA (US)

(*) Notice: Subject to any disclaimer, the term of this patent is extended or adjusted under 35 U.S.C. 154(b) by 9 days.

(21) Appl. No.: 09/824,299

(22) Filed: Apr. 2, 2001

(65) Prior Publication Data

US 2002/0143270 A1 Oct. 3, 2002

(51) Int. Cl.⁷ .............................................. A61B 10/00
(52) U.S. Cl. ..................................................... 600/565
(58) Field of Search ................................. 600/565, 593, 600/568; 604/22, 119, 248, 902; 606/170, 180, 45, 49, 159, 200; 128/898; 137/625.22; 30/29.5

(56) References Cited

U.S. PATENT DOCUMENTS

| | | | |
|---|---|---|---|
| 4,651,753 A | | 3/1987 | Lifton |
| 4,735,605 A | * | 4/1988 | Swartz ....................... 600/568 |
| 4,775,365 A | * | 10/1988 | Swartz ....................... 604/119 |
| 4,932,935 A | * | 6/1990 | Swartz ....................... 604/22 |
| 5,381,800 A | * | 1/1995 | Angelchik ................. 128/898 |
| 5,542,432 A | | 8/1996 | Slater et al. |
| 5,569,178 A | * | 10/1996 | Henley ........................ 604/22 |
| 5,601,585 A | | 2/1997 | Banik et al. |
| 5,762,069 A | | 6/1998 | Kelleher et al. |
| 5,810,744 A | | 9/1998 | Chu et al. |
| 5,823,971 A | | 10/1998 | Robinson et al. |
| 5,921,943 A | | 7/1999 | Kass |
| 5,928,164 A | | 7/1999 | Burbank et al. |
| 5,941,876 A | * | 8/1999 | Nardella et al. .............. 604/22 |
| 5,964,716 A | | 10/1999 | Gregoire et al. |
| 5,980,468 A | | 11/1999 | Zimmon |
| 5,980,469 A | | 11/1999 | Burbank et al. |
| 6,019,733 A | | 2/2000 | Farascioni |
| 6,019,758 A | | 2/2000 | Slater |
| 6,024,751 A | * | 2/2000 | Lovato et al. ................ 604/22 |
| 6,050,955 A | | 4/2000 | Bryan et al. |
| 6,053,877 A | | 4/2000 | Banik et al. |
| 6,071,248 A | | 6/2000 | Zimmon |
| 6,309,399 B1 | * | 10/2001 | Barbut et al. ................ 606/159 |

OTHER PUBLICATIONS

"Colonoscopic Polypectomy and Therapeutic Procedures" pp. 224–242.

* cited by examiner

*Primary Examiner*—Max F. Hindenburg
*Assistant Examiner*—Brian Szmal
(74) *Attorney, Agent, or Firm*—RatnerPrestia

(57) ABSTRACT

A device for obtaining multiple biopsy samples from a body cavity is provided, comprising: a flexible hollow tube having a sample port; a moveable helical cutting element extending within the tube, wherein the cutting element is capable of severing, entrapping and carrying forward multiple biopsy samples; a means for maneuvering the cutting element along the tube; a removable seal secured to the distal end of the tube; and a vacuum port configured to be connected to a vacuum source.

13 Claims, 3 Drawing Sheets

MULTIPLE BIOPSY DEVICE

FIELD OF THE INVENTION

This invention relates to medical biopsy instruments. More specifically, this invention relates to devices used in conjunction with an endoscope, for retrieval of multiple biopsy samples from a body cavity.

BACKGROUND OF THE INVENTION

Biopsy devices that have been developed in the past include forceps, non-endoscopic devices, and single as well as multiple biopsy sample devices. The disadvantage with many of these devices, with the exception of multiple sample devices, is that the device must be withdrawn from patient after a single biopsy sample is obtained. In addition, many devices of the past have been awkward and uncomfortable for the patient.

Multiple biopsy devices that have been developed, although beneficial in the sense that multiple samples can be obtained without removing the device from the body, do not offer benefits of receiving multiple samples and storing them segregated from each other in the order in which they were obtained. Moreover, identification of the precise location from which the biopsy sample was obtained is difficult. These and other advantages are obtained by the multiple biopsy device of this invention.

SUMMARY OF THE INVENTION

In accordance with the present invention, a device for obtaining multiple biopsy samples from a body cavity is provided. The device comprises: a flexible hollow tube having a side sample port through the wall of the tube; a moveable helical cutting element within the tube, wherein the cutting element is configured to sever, entrap and carry multiple biopsy samples along the tube into a storage/retrieval area beyond the sample port; means for moving the helical cutting element along the tube; a removable seal secured to the distal end of the tube; and a vacuum port positioned at the proximal end of the device, said vacuum port configured to communicate with a vacuum source.

The device is constructed such that the sample port of the tube can be precisely aligned with and in close proximity to the tissue to be sampled on the walls of a body cavity, utilizing an endoscope as a visual tool to facilitate alignment. The present device may be used in conjunction with a variety of flexible endoscopes. The helical cutting element is advanced toward the distal end such that a first cutting/receiving area on the cutting element is in alignment with the sample port. The sample is drawn into the tube under vacuum suction, and the helical cutting element is advanced to sever and entrap the sample in the receiving area of the helix. The helical cutting element is then advanced to a subsequent cutting/receiving area with a forward motion. The helical cutting element cuts the biopsy sample during the procedure; entraps the sample in the area between adjacent coils of the helix; and pushes forward the collected samples into a storage area of the tube. This permits the collection of multiple samples without removing the device from the body cavity. The spiral or helical cutting element is also advantageous in receiving the samples, separating them from each other, and holding them in the order in which they were severed and collected. Thus, the integrity of the samples is maintained, and identification of the area from which the sample was obtained is made possible.

DETAILED DISCUSSION OF THE INVENTION

Figure 1:
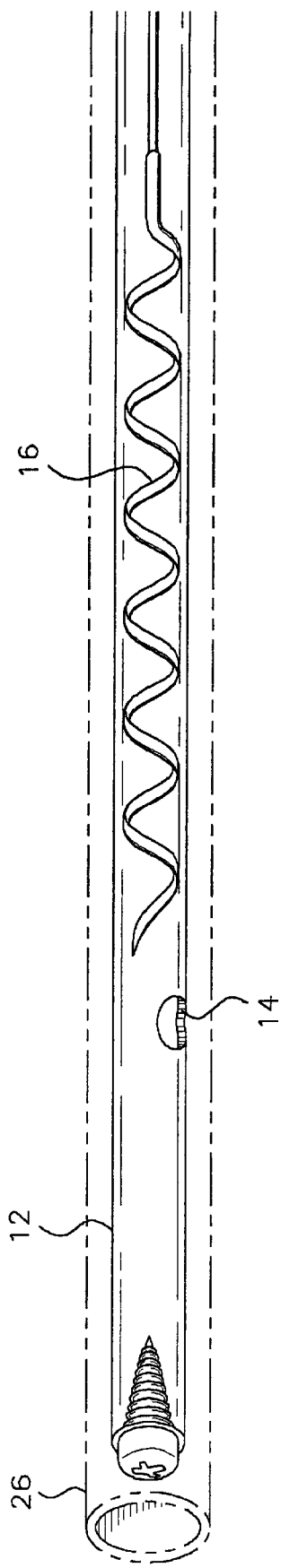
FIG. 1 is a side perspective view of the biopsy tube inserted into an endoscopic biopsy channel.
Figure 2:
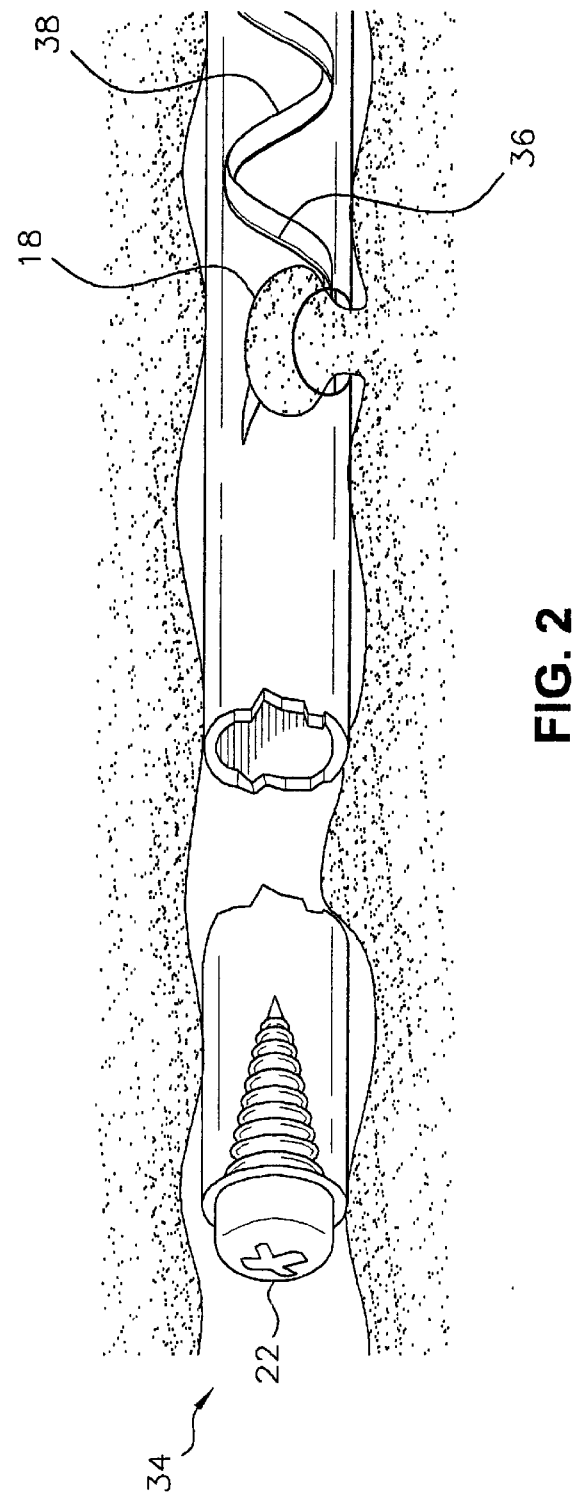
FIG. 2 shows the helical cutting element in position for collection of first sample.

In accordance with the present invention, a device for obtaining multiple biopsy samples from a body cavity is provided as shown in FIGS. 1 & 2. The device comprises: a flexible hollow tube 12 having a side sample port 14 in the wall of the tube, a moveable helical cutting element 16 within the tube 12, wherein the helical cutting element is configured to sever, entrap and carry a multitude of biopsy samples 18 along the tube 12; means 20 for moving the helical cutting element along the tube; a removable seal 22 secured to the distal end 34 of the tube 12; and a vacuum port 24 at the proximal end 30 and configured to communicate with a vacuum source 32 and, via the channel of the tube 12, with the sample port 14.

Uses for the present invention include biopsies within body cavities especially for sampling of polyps and other tissue material. Biopsy samples refer to samples of tissue, polyps, mucosa, and any matter that is in the wall of a body cavity that needs to be removed for examination or to be discarded. Areas of the body which are viable candidates for use of this instrument in obtaining biopsy samples include, for example, the gastrointestinal tract, urinary tract, bronchial tract, blood vessels, and regions of the heart.

Biopsy samples obtained in the present invention include those, are of a predetermined size sufficient to enable the helical cutting element 16 to entrap and hold the sample. The biopsy samples should have a size large enough to be securely held in place by the helical cutting element 16. The biopsy samples are preferably slightly larger than the internal diameter of the helical cutting element. Thus, the sample port 14 is suitably sized to a diameter sufficient to allow a sample of that size to be drawn in under a moderate vacuum. Biopsy samples which are smaller in size than the diameter of the helical cutting element 16 may be obtained and, will nonetheless be carried forward to the storage area 28 of the device when the helical cutting element 16 is advanced beyond the sample port 14. It is noted that even such smaller samples are unaffected by the vacuum suction. Thus they remain in the tube in the order in which they are obtained. That is, the air beyond the sample port is quiescent and thus does not subject samples in the storage area to the subsequent application of the vacuum.

In order to ensure that a biopsy sample 18 is of sufficient size for the present application, it is desirable that the distance between successive coils of the helix 16 be at least equal to the longitudinal diameter of the sample port 14. This relationship permits a biopsy sample 18 of sufficient size to be entrapped by the helical cutting element 16. Thus, the helical cutting element 16 cuts and firmly holds the biopsy sample 18 within its coils.

Figure 4:
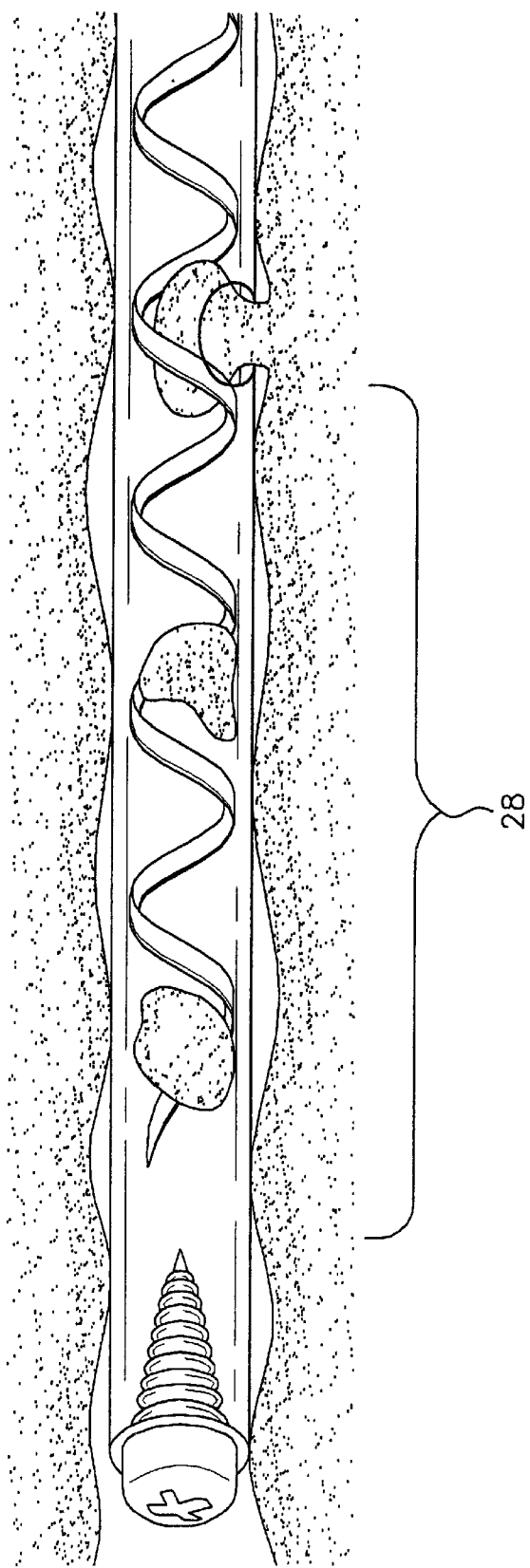
FIG. 4 is a perspective view illustrating the collection of multiple samples.

As shown in FIG. 4, multiple samples are kept within the coils in the order in which they are obtained. As many as 20 to 30 or more samples may be obtained using the present device. The number of biopsy samples which are obtained in a single pass, depends proportionally on the length of the helical cutting element 16, i.e., the number of coils of the helical cutting element 16, and the length of the storage area 28 of the tube 12. For example, a helix with multiple coils will be able to hold as many samples as the number of coils. The collected samples will be held in the storage area 28 of the tube 12, thus the length of the storage area will also dictate the number of samples that may be obtained. FIG. 4 also shows the helical cutting element 16 progressing into the storage area 28 of the tube, once the multiple biopsy samples have been obtained.

An endoscope may be used in conjunction with the device in order to aid the device in navigating through the body cavity. A flexible variety of the endoscope is preferred, especially in the use for example in the gastrointestinal tract. Other areas of use include other body cavities that require a flexible instrument for easier penetration. The endoscope device typically has a length of about 100–250 cm and a channel diameter of 2.0–3.8 mm. The tube of the present invention works by placing it through the biopsy channel of an endoscope until it can be seen endoscopically. Thus the tube 12 must have a diameter slightly smaller than the endoscopic biopsy channel 26 with which it is used and must be of sufficient length to allow it to protrude through the distal end of the endoscopic biopsy channel 26. This protrusion must be sufficient such that the sample port 14 of the tube 12 extends beyond the end of the endoscope to permit visual alignment of the sample port 14 and the sample 18 to be taken.

The aid of the endoscope also permits marking or noting of the precise 30 location from which the biopsy sample 18 is obtained. Thus, visually marking the territory from which the first, second, third, etc. samples 18 are obtained makes it possible to distinguish the samples once they are withdrawn from the storage area 28 of the tube 12. For example, when polyps are collected from the gastrointestinal tract, noting the precise area from which the first, second, third, etc. polyp was severed aids in identifying the samples once they are removed from the tube. The present invention's use of the helical cutting element 16 keeps the samples 18 separate and in the order which they were retrieved. In addition, integrity of the collected samples is maintained.

The hollow tube 12 of the present invention is flexible to allow for easy penetration, even into the most obscure areas of the body. The flexible tube or catheter may preferably be made of plastic, however, any material which allows the capability of flexing is acceptable. The size of the tube, specifically its diameter and length depends on the ultimate use of the device. The device can be configured according to the body cavity and may also be configured according to the instruments used in conjunction with the biopsy device of the present invention. For example, the diameter of the tube will be less than the diameter of the endoscopic biopsy channel 26.

The proximal end 30 of the tube is provided with a vacuum port 24 which is adapted for connection, for example via vacuum tube 32 with a vacuum source (not shown). The vacuum source provides suction for drawing the biopsy sample 18 into the side sample port 14. Any suitable suction means may be used for this purpose, including for example, a syringe, a Gomco suction, or wall suction. These suction devices and methods for their use in connection with certain prior art biopsy devices are known in the art.

The distal end 34 of the tube has a removable seal 22 secured when the device is in operation, especially, for instance, when the vacuum suction is applied. The seal 22 is removed when the device is retracted from the body cavity and the samples 4 are ready to be removed for inspection. The seal 22 may be a removable screw, cap or plug, which acts as a vacuum seal and prevents the cutting device from exiting the distal end of the tube until the seal is removed. By removing the screw, the helical cutting device 16 can be pushed out of the tube 12 after biopsy specimens 18 are taken and the biopsy specimens can be placed, for example, in formalin fixative for subsequent examination or testing.

Since a vacuum source allows for the biopsy sample 18 to be drawn in through the sample port 14, the moving means must also be attached such that the entire apparatus is air sealed. For example, in order to air seal the plunger, a Toomy-Borsh like adapter 40 may be used around the plunger.

In a preferred embodiment of the present invention, the configuration of the helical cutting element is a spiral or helical coil as shown in FIGS. 1, 2, and 4. The internal diameter of the coil along its trailing surface is such that it will entrap the severed sample and carry it forward in the tube as the cutting element is advanced toward the distal end of the tube to the next sampling position on the cutting element. Thus, those skilled in the art will recognize that there is a relationship between the size, i.e. diameter, of the sample port, the amount of suction applied, the size of the severed sample and the internal diameter of the cutting element. It will also be appreciated by those skilled in this art that the cutting element of the present invention is preferably a coil or helix, it need not be limited to a coil or helical shape, but may include any equivalent configuration which enables the cutting tool to sever, entrap and carry multiple is biopsy sample along the longitudinal axis of the tube separated from each other in the order in which the samples are taken.

The spiral cutting element 16 has a leading, sharp cutting edge 36 and a trailing edge 38. The cutting edge 36 may be sharp along its entire leading edge, or may be sharp at intervals. The trailing edge 38 is configured to entrap and hold the severed sample 18. The entire helical cutting element 16 is capable of being pushed forward, in order to carry the sample forward toward and eventually into the storage area 28 of the tube.

The cutting edge 36 severs a biopsy sample upon forwardly advancing the spiral cutting element 16. A plunger 20 attached to the spiral cutting 25 element may be used to maneuver the spiral or cutting tool forward. Once the biopsy sample 18 is drawn in through the sample port 14, with the aid of vacuum suction 32, the cutting element 16 is advanced sufficiently to sever the biopsy sample 18. A configuration such as the spiral, entraps or holds the sample and maintains a firm grip on the biopsy sample as the helical cutting element 16 is progressed along the tube 12. FIG. 4 shows multiple samples of biopsy 18 held by the spiral cutting element 16, thus maintaining a grip on the samples that were obtained, keeping them in the order in which they were obtained.

Figure 3:
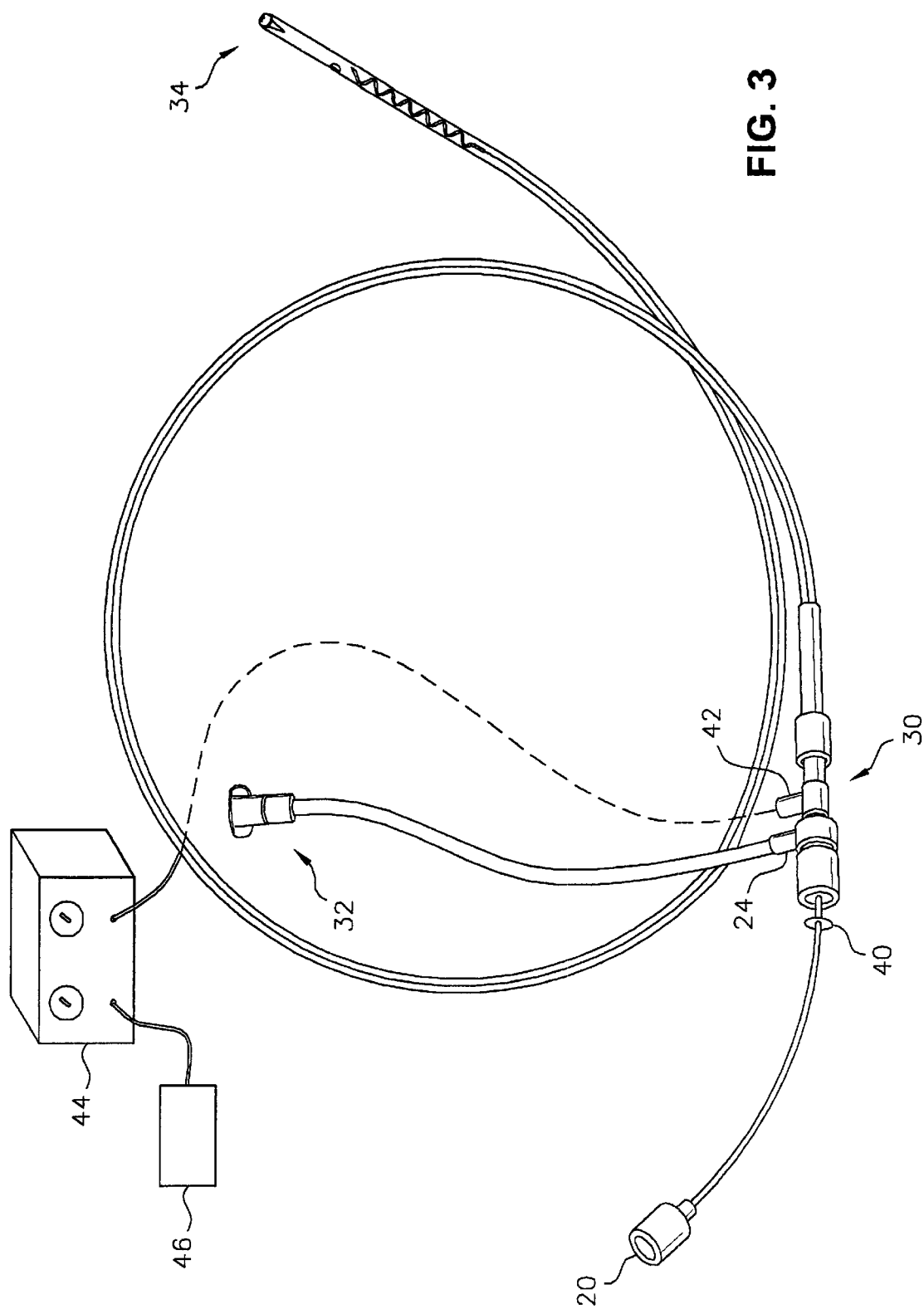
FIG. 3 is a perspective overview of one embodiment of the device.

In the foregoing embodiment, the cutting element is a mechanical means for cutting the desired samples. In another embodiment, as shown in FIG. 3, the helical element 16 may be an electrical cutting element operated by the use of a monopolar current device 44. For application in this embodiment, an electrosurgical unit 44 is attached to the device of the present invention, the unit having circuitry to cut, coagulate and a blend of the two. These units are well known in the art and this procedure is sometimes referred to as hot biopsy. For practice of this embodiment the electrosurgical unit 44 is connected to an electrical conductor shown for example and generally at location 42 which conducts electrical current between the unit and the element 16 within the tube 12. A grounding pad 46 is also connected to the electrosurgical unit 44 and placed on the patient. Current is then applied through the device, enabling the cutting element 16 to coagulate and cut the biopsy sample 18. The type of current that is used depends on whether the goal of the procedure is to cut the tissue sample or coagulate it. It will be appreciated by those skilled in the art that this embodiment may be used to simply coagulate samples which have been mechanically cut by the cutting element 16.

The method for obtaining multiple biopsy samples 18 from a body cavity, comprises the steps of: providing the device of the present invention; inserting the flexible hollow tube 12 through an endoscopic biopsy channel 26 that is placed in a body cavity; positioning the tube 12 such that the sample port 14 is proximal to and aligned with the biopsy sample 18; applying a suction from the vacuum source 32 wherein the suction draws the biopsy sample 18 through the sample port 14; advancing the helical cutting element 16 in a forward motion until the biopsy sample 18 is obtained; and repositioning the device for obtaining subsequent biopsy samples as shown in FIG. 4. A monopolar device 44 may also be used to activate the helical element 16 within the tube 12.

What is claimed is:

1. A device for obtaining multiple biopsy samples from a body cavity, comprising:
    a flexible hollow tube having a sample port in a wall of said tube, said sample port positioned toward a distal end of said tube and having a diameter sufficient to draw into the tube a biopsy sample of predetermined size;
    a sample storage area in said tube distal to said sample port;
    a helical cutting element within the tube, movable along the longitudinal axis of the tube to sever and hold multiple biopsy samples and advance such severed samples into said sample storage area in the order in which the samples are severed;
    means for moving the helical cutting element along the longitudinal axis of the tube into alignment with the sample port and advancing severed samples retained in the coils of the helix cutting element along said axis into said storage area;
    a removable seal at the distal end of said tube; and
    a vacuum port at the proximal end of the tube communicating with an interior of said tube, whereby the sample is drawn through the sample port into the interior of the tube.

2. The device of claim 1, wherein the distance between adjacent coils of the helical cutting element is at least equal to the longitudinal diameter of said sample port.

3. The device of claim 1, wherein the space between successive coils of the helical cutting element define sample receiving areas of said helical cutting element.

4. The device of claim 1 wherein the helical cutting element has a sharp leading edge.

5. The device of claim 1 wherein the internal diameter of the helical cutting element is slightly less than the diameter of the sample port.

6. The device of claim 2, wherein the leading edge is sharp at intervals.

7. The device of claim 1, wherein the means for moving the helical cutting element comprises a plunger.

8. The device of claim 1, wherein an outer diameter of the tube is adapted for insertion into a body cavity through an endoscopic biopsy channel.

9. The device of claim 1, wherein the helical cutting element is activated by a monopolar current device.

10. The device of claim 7, wherein the activated helical cutting element cuts and coagulates the biopsy sample.

11. A device for obtaining multiple biopsy samples from a body cavity, comprising:
    a flexible hollow tube having a sample port in the wall of said tube, said sample port having a diameter sufficient to draw into the tube a biopsy sample of predetermined size;
    a sample storage area in said tube distal to said sample port;
    an electrically conductive helical cutting element extending within the tube, movable along the longitudinal axis of the tube to sever and hold multiple severed biopsy samples and advance such samples into said sample storage area in the order in which samples are severed;
    a monopolar current device in communication with the helical element;
    means for moving the helical element along the longitudinal axis of the tube, into alignment with said sample port and advancing severed samples retained in the coils of the cutting element along said axis into said storage area;
    a removable seal at the distal end of the tube; and
    a vacuum port on the tube, wherein the vacuum port is configured to communicate with a vacuum source wherein the biopsy sample is drawn into the tube through the sample port and severed by advancing said cutting element along said longitudinal axis.

12. A method for obtaining multiple biopsy samples from a body cavity, comprising the steps of:
    (a) providing a flexible hollow tube having a sample port of a diameter sufficient to draw into the tube a biopsy sample of predetermined size; a sample storage area in said tube distal to said sample port; a moveable helical cutting element extending within the tube; a means for moving the helical cutting element along the longitudinal axis of said tube; a removable seal secured to the distal end of said tube; and a vacuum port proximal to said sample port of the tube, wherein the vacuum port is configured to communicate with a vacuum source;
    (b) inserting the flexible hollow tube through an endoscopic biopsy channel that is placed in a body cavity;
    (c) positioning the tube such that the sample port is aligned with a biopsy sample;
    (d) applying a suction from the vacuum source, wherein the suction draws the biopsy sample through the sample port into the tube;
    (e) advancing the helical cutting element along the longitudinal axis of tube until the biopsy sample is obtained; and
    (f) advancing the sample into the sample storage area and repositioning the tube for obtaining subsequent biopsy samples.

13. A method for obtaining multiple biopsy samples from a body cavity, comprising the steps of:
    (a) providing a flexible hollow tube having a sample port of a diameter sufficient to draw into the tube a biopsy sample of predetermined size; a sample storage area in said tube distal to said sample port; a moveable helical electrically conductive cutting element extending within the tube, wherein the cutting element is in communication with a monopolar current device; a means for moving the helical conductive cutting element along longitudinal axis of the tube; a removable seal secured to the distal end of said tube; and a vacuum port at the proximal end of the tube, wherein the vacuum port is configured to communicate with a vacuum source;

(b) inserting the flexible hollow tube through an endoscopic biopsy channel that is placed in a body cavity;

(c) positioning the tube such that the port is aligned with a biopsy sample;

(d) applying a suction from the vacuum source, wherein the suction draws the biopsy sample through the sample port and into the tube;

(e) sending an electrical current through the helical conductive element to sever the biopsy sample;

(f) advancing the helical conductive element in a forward motion along the longitudinal axis of the tube until the biopsy sample is obtained; and (g) advancing the sample into the sample storage area and repositioning the tube for severing subsequent biopsy samples.

* * * * *